(12) United States Patent
Windorfer

(10) Patent No.: US 10,247,669 B2
(45) Date of Patent: Apr. 2, 2019

(54) DEVICE FOR PROCESSING A SURFACE

(71) Applicant: Vorwerk & Co. Interholding GmbH, Wuppertal (DE)

(72) Inventor: Harald Windorfer, Mettmann (DE)

(73) Assignee: Vorwerk & Co. Interholding GmbH, Wuppertal (DE)

( * ) Notice: Subject to any disclaimer, the term of this patent is extended or adjusted under 35 U.S.C. 154(b) by 0 days.

(21) Appl. No.: 15/554,560

(22) PCT Filed: Jan. 11, 2016

(86) PCT No.: PCT/EP2016/050337
§ 371 (c)(1),
(2) Date: Aug. 30, 2017

(87) PCT Pub. No.: WO2016/116309
PCT Pub. Date: Jul. 28, 2016

(65) Prior Publication Data
US 2018/0164213 A1 Jun. 14, 2018

(30) Foreign Application Priority Data
Jan. 23, 2015 (DE) .................. 10 2015 100 977

(51) Int. Cl.
*G01N 21/55* (2014.01)
*G01N 21/25* (2006.01)
(Continued)

(52) U.S. Cl.
CPC ............ *G01N 21/55* (2013.01); *A47L 9/2805* (2013.01); *G01N 21/251* (2013.01);
(Continued)

(58) Field of Classification Search
CPC .............. A47L 11/4011; A47L 11/4061; A47L 2201/06; A47L 9/30; A47L 9/2805;
(Continued)

(56) References Cited

U.S. PATENT DOCUMENTS 5,650,702 A 7/1997 Azumi
5,864,394 A 1/1999 Jordan, III et al.
(Continued)

FOREIGN PATENT DOCUMENTS

EP 1 241 465 A1 9/2002
EP 1 494 017 A1 1/2005
(Continued)

OTHER PUBLICATIONS

International Search Report of PCT/EP2016/050337, dated May 10, 2016.

*Primary Examiner* — Tri T Ton
(74) *Attorney, Agent, or Firm* — Collard & Roe, P.C.

(57) ABSTRACT

A cleaning robot has an optical measuring device for determining the type of surface to be cleaned. The optical measuring device has a light source and at least two light sensors. Light emitted by the light source hits a reflection point of the surface at an angle of incidence ($\alpha$), and is reflected to the first light sensor at a corresponding angle of reflection ($\beta$). The light source, reflection point and first light sensor span a plane of incidence. A secondary plane that intersects the reflection point and has a second light sensor spans perpendicular to the surface, and exhibits an angle ($\delta$) of between 80° and 100° relative to the plane of incidence. A straight line running through the reflection point and second light sensor has an angle ($\gamma$) relative to the surface that is essentially as large as the angle of incidence ($\alpha$) or angle of reflection ($\beta$).

4 Claims, 2 Drawing Sheets

(51) Int. Cl.
*A47L 9/28* (2006.01)
*G01N 21/47* (2006.01)

(52) U.S. Cl.
CPC ........... *G01N 21/255* (2013.01); *G01N 21/47* (2013.01); *A47L 2201/06* (2013.01); *G01N 2021/4726* (2013.01); *G01N 2021/4735* (2013.01); *G01N 2021/555* (2013.01); *G01N 2021/556* (2013.01)

(58) Field of Classification Search
CPC ......... G05D 1/0274; G05D 2201/0203; F02M 51/066; F02M 51/0685; F02M 61/08; F02M 67/12; Y10T 137/87668; Y10T 137/87772; G01N 21/55; G01N 21/255; G01N 21/47; G01N 2021/4726; G01N 2021/4735; G01N 2021/555; G01N 2021/556
USPC .......... 356/445–448, 600–613, 237.1–237.6, 356/239.1–239.8
See application file for complete search history.

(56) References Cited

U.S. PATENT DOCUMENTS

| | | | |
|---|---|---|---|
| 7,224,446 | B2 | 5/2007 | Kreh et al. |
| 9,629,514 | B2 | 4/2017 | Hillen et al. |
| 2005/0168729 | A1 | 8/2005 | Jung et al. |
| 2009/0257058 | A1 | 10/2009 | Urano et al. |
| 2012/0006352 | A1* | 1/2012 | Holappa ................. B08B 1/008 134/6 |
| 2012/0169497 | A1* | 7/2012 | Schnittman ............. A47L 9/106 340/540 |

FOREIGN PATENT DOCUMENTS

| | | |
|---|---|---|
| EP | 1 677 099 A1 | 7/2006 |
| EP | 2 741 483 A2 | 6/2014 |
| JP | 2002-174595 A | 6/2002 |
| JP | 2006-105774 A | 4/2006 |

* cited by examiner

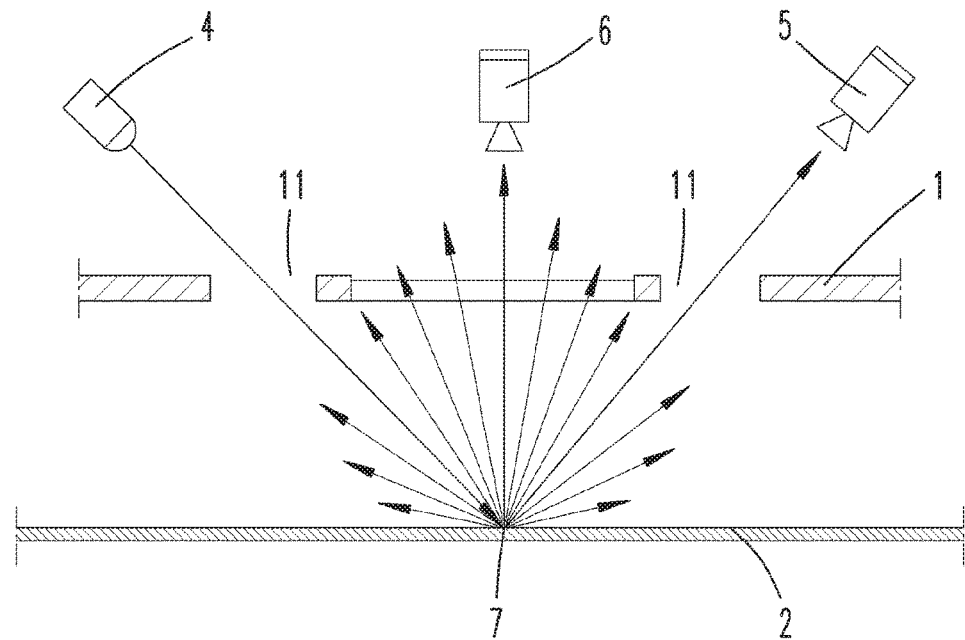
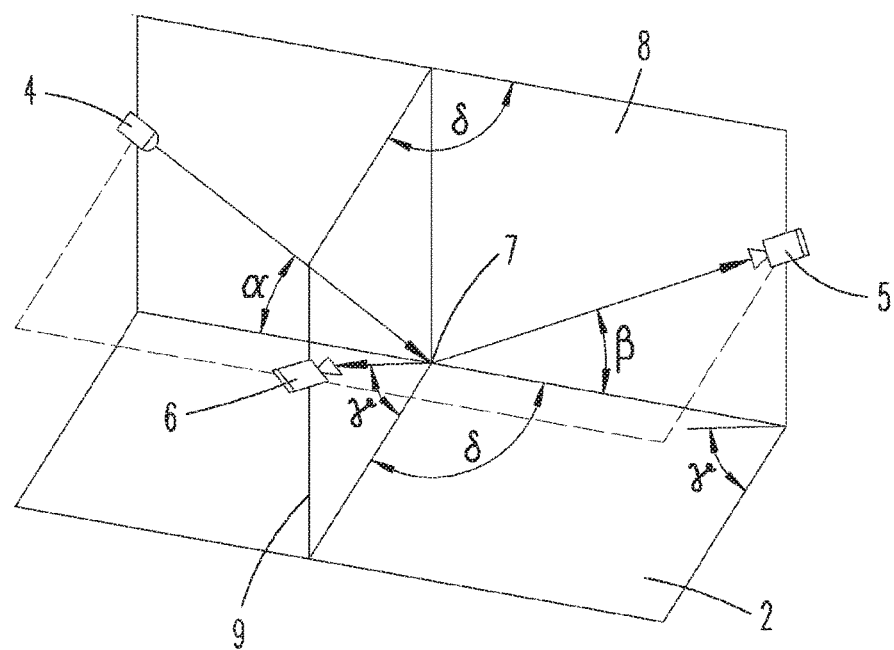

DEVICE FOR PROCESSING A SURFACE

CROSS REFERENCE TO RELATED APPLICATIONS

This application is the National Stage of PCT/EP2016/050337 filed on Jan. 11, 2016, which claims priority under 35 U.S.C. § 119 of German Application No. 10 2015 100 977.3 filed on Jan. 23, 2015, the disclosures of which are incorporated by reference. The international application under PCT article 21(2) was not published in English.

BACKGROUND OF THE INVENTION

The invention relates to a device, in particular to a cleaning robot, for processing a surface, wherein the device has an optical measuring device for determining the type of surface.

Devices of this kind are sufficiently known in prior art. Involved here, for example, are vacuuming or wiping robots, which can autonomously traverse a surface to be cleaned, and thereby perform cleaning tasks such as vacuuming, wiping or the like. In order to adjust the type of processing to the respective type of surface, an optical measuring device is provided, which first determines the type of surface prior to the processing operation. As a result, for example, specific areas of a room are excluded from processing, because their surface is not suitable for that purpose. For example, it can be provided for a wiping robot that carpets be excluded from wet cleaning. In addition, for example, the fan power and brushing power can be adjusted to the respective surface in a vacuuming robot. In like manner, sealing lips or support rollers can be adjusted as a function of the respective surface.

Various optical measuring devices are known in prior art for determining the type of surface. Imaging measuring devices are often used, which utilize a camera system to record an image of the surface, and compare it to reference images or reference features. The technical outlay for the camera system along with the image processing for evaluating the image is correspondingly high. Also known are gloss meters, in which the gloss of the surface is measured. The disadvantage here is that these measuring devices only deliver a reliable measuring result if the surface to be measured has been completely sealed off from ambient light. In this regard, such a measuring device requires a higher expenditure of equipment.

SUMMARY OF THE INVENTION

Therefore, the object of the invention is to create a surface processing device with an optical measuring device for determining the type of surface that makes it possible to reliably determine the type of surface with little technical outlay.

As a solution, the invention proposes a device for processing a surface in which the optical measuring device has a light source and at least two light sensors, wherein the light source and a first light sensor are arranged in such a way that light emitted by the light source hits a reflection point on the surface at an angle of incidence, and is then reflected to the first light sensor at a corresponding angle of reflection, wherein the light source, the reflection point and the first light sensor span a plane of incidence, and wherein a secondary plane that intersects the reflection point and has a second light sensor spans perpendicular to the surface, and exhibits an angle of between 80° and 100° relative to the plane of incidence, wherein a straight line running through the reflection point and the second light sensor has an angle relative to the surface that is essentially as large as the angle of incidence or angle of reflection.

According to the invention, the first light sensor and second light sensor are now used to measure various light intensities, wherein the first light sensor measures the light component of the light emitted by the light source that is reflected by the reflection point, and the second light sensor measures a diffusely scattered light component. The scattered light component can here be both a component of the light radiated by the light source onto the reflection point (in particular if the surface is not smooth) as well as a component of the ambient light (for example, the ceiling lights in a room). The optical measuring device set up in this way is suitable overall for implementing a measuring method according to the so-called Phong illumination model, which evaluates intensities measured by the light sensors under different conditions. The Phong illumination model is an illumination model used for 3D computer graphics to calculate an illumination of objects. The Phong model is known for calculating the illumination of smooth surfaces, wherein it was surprisingly discovered within the framework of the invention that this model is also suitable for differentiating between smooth and non-smooth surfaces. This illumination model does involve an empirical model that is essentially not based upon physical principles. Nonetheless, it is suitable for reliably distinguishing between surface types.

According to the invention, the optical measuring device is here set up in such a way that the light components taken into account based upon the Phong illumination model can be measured. On the one hand, this includes the light component of the emitted light reflected at the reflection point. The light source, the reflection point and the first light sensor span the plane of incidence, while the second light sensor and the reflection point are arranged in a secondary plane perpendicular thereto, which also stands perpendicular to the surface. The secondary plane and the plane of incidence span an angle of between 80° and 100°. Let it here be observed that the first light sensor and the second light sensor are arranged at the same angle relative to the surface, so that the light components measured by the first or second light sensor are comparable to each other in terms of their intensity. In particular, it is recommended that the first light sensor and the second light sensor have the same distance to the reflection point. As a result, the measuring accuracy can be further increased. In particular, the first light sensor and the second light sensor can be arranged in a shared plane that is parallel to the surface. The light source is advantageously also in the same plane, so that the measuring setup can be adjusted especially easily and quickly. In particular, this facilitates a fast and cost-effective manufacture of the optical measuring device, and hence of the processing device.

It is recommended that the angle of incidence, the angle of reflection and the angle of the second light sensor relative to the surface each measure between 30° and 45°. In this way, the light emitted by the light source of the optical measuring device can be distinguished from an ambient lighting, for example the ceiling lights in a room, since the ambient light usually has a higher angle of incidence relative to the surface.

It is recommended that the angle between the plane of incidence and the secondary plane measure 90°. This angle can here also have a slight deviation of several degrees without significantly influencing the measuring result. However, an accuracy of +/−3° is the target. The perpendicular alignment of the plane of incidence and secondary plane relative to each other makes it possible to differentiate between the light reflected by the reflection point and the scattered light that is basically scattered in all directions.

The intensities of the light components reflected or scattered by the surface are advantageously measured with two light sensors. For example, the light sensors can be photodiodes, camera chips or the like. The sensors are aligned at the same angle to the illuminated surface, wherein the first light sensor is arranged precisely opposite the light source relative to the reflection point, so that the light is reflected directly onto the first light sensor given a smooth surface under the condition "angle of incidence equals angle of reflection". The second light sensor is directed toward the reflection point at just as large an angle to the surface, but in the secondary plane turned by approx. 90° in relation to the plane of incidence.

In terms of determining the type of surface by means of the Phong illumination model, the device as a whole is designed in such a way that various light components can be measured using the light sensors in sequential measuring steps. The measured light intensities are advantageously evaluated with an evaluator of the device according to the invention, wherein the measurement and evaluation are based on the assumption that the light intensity as a whole is comprised of the ambient light, the diffusely scattered light and the reflected light, i.e., according to the mathematical equation $$I_{ambient} + I_{diffuse} + I_{reflected} = I_{total}$$

A measuring cycle of the device here comprises the following three measuring steps:
1. Measuring $I_{ambient}$ with the first light sensor and the second light sensor with the light source turned off.
2. Measuring $I_{ambient} + I_{diffuse} + I_{reflected}$ with the first light sensor with the light source turned on.
3. Measuring $I_{ambient} + I_{diffuse}$ with the second light sensor with the light source turned on.

Proceeding from the measured light intensities, the evaluator of the device can infer the type of currently measured surface from a comparison with corresponding reference intensities for known surfaces.

In addition, it is proposed that the light source be a polychromatic light source, in particular a white light source. The polychromatic light source emits light components of varying wavelengths, which can be evaluated independently of each other. A first evaluation can thus be performed in relation to a first wavelength, a second evaluation in relation to a second wavelength, etc. Since the surface to be measured potentially reflects light of varying wavelength with a varying reflectance, additional information can in this way be obtained bout the surface to be determined.

In this conjunction, it is recommended that the light sensors be wavelength selective in design. In particular, the light sensors can be RGB sensors or non-wavelength selective sensors, for example photodiodes, which are equipped with corresponding filters, so that the light components of varying wavelength can be detected separately from each other.

In this conjunction, there are various potential measuring devices. For example, in a first possible device, a white light source can emit light that is reflected to the reflection point of the surface and then divided by an RGB sensor into the wavelength components red, green and blue. Alternatively, several non-wavelength selective photodiodes can be arranged next to each other, wherein a spectral filter is allocated to each photodiode, and differs from the spectral filters of the other photodiodes. In another device, the light source can additionally be a pulsed RGB light source, which emits light of varying wavelengths in chronologically sequential time intervals. During a first timespan, for example, a red light component is emitted, which hits the light sensor, followed in a second timespan by a green light component and in a third timespan by a blue light component. This measuring sequence can subsequently be repeated. The evaluator of this device can allocate corresponding information about the wavelength emitted in the respective timespan to the measured intensities. The frequency at which the measuring cycle repeats depends on the type of used light source and the light sensors. For example, a measuring cycle can take only a few milliseconds.

In addition to the device described above for processing a surface, the invention likewise proposes a method for processing, in particular cleaning, a surface by means of a device, wherein the device determines the type of surface with an optical measuring device and adjusts the type of processing as a function thereof. In particular, the method can be implemented using a device proposed before. According to the invention, light inside of a plane of incidence is radiated at an angle of incidence from a light source onto a reflection point of the surface, and from there reflected with a corresponding angle of reflection to a first light sensor, wherein a second light sensor is arranged in a secondary plane that stands perpendicular to the surface, intersects the reflection point, and has an angle of between 80° and 100° to the plane of incidence in such a way that a straight line running through the reflection point and the second light sensor has an angle to the surface that is essentially as large as the angle of incidence or the angle of reflection.

In order to determine the type of surface, it is proposed that the following measuring steps be implemented in any sequence desired: Measuring the light intensity with the first light sensor and the second light sensor with the light source turned off, measuring the light intensity with the first light sensor with the light source turned on, and measuring the light intensity with the second light sensor with the light source turned on. In this way, a total of three different intensities are measured within a measuring cycle. In the first mentioned step, the light source is turned off and the diffuse scattered light is measured based on the ambient lighting. This yields:

$$I_{ambient} = I_1 = I_2$$

During another measuring step, the light source is turned on, and the first light sensor measures the overall intensity from the scattered light of the environment, the scattered light of the light source and the reflected light component of the light source. This yields:

$$I_3 = I_{total} = I_{ambient} + I_{diffuse} + I_{reflected}$$

During another measuring step, the second light sensor measures the ambient light and the scattered light of the light source with the light source turned on. This yields:

$$I_4 = I_{ambient} + I_{diffuse}$$

The resultant equation system can be resolved as follows:

$$I_{diffuse} = I_4 - I_1$$

$$I_{reflected} = I_3 - I_4$$

As a consequence, the three steps make it possible to measure the current light intensities of the scattered light and the reflected light on the surface to be determined. These provide information about the type of surface.

It is proposed that the light intensities measured by the light sensors be compared with corresponding reference intensities for known surfaces. The reference intensities are here advantageously stored in a memory of the device according to the invention, so that they are available to the evaluator for a comparison with the measured light intensities. If a measured light intensity corresponds to a stored reference intensity, the type of surface may be inferred. The reference intensities were advantageously measured with the same optical measuring device or at least with a similar measuring device, so that the reference intensities can be compared with the currently measured light intensities. The device, for example a cleaning robot, can advantageously be placed inside of a home to record reference intensities on varying surfaces, wherein a measuring cycle is performed, and information about the type of measured surface is manually stored in the memory of the device. For example, if a measurement was conducted in a carpeted area of the room, the user of the cleaning robot can allocate the information that the measured surface is a carpet to the stored light intensities, i.e., to the scattered light intensity and reflected light intensity. The same thing can then be done with other areas of the room, which have tile, parquet, cork, laminate, PVC or other floorings.

It is further proposed that the light source emit polychromatic light, thereby—as explained above—resulting in intensity values for various light wavelengths that are independent of each other, which in turn make it possible to more precisely determine the measured type of surface.

Finally, it can be provided that the light that gets from the surface to the light sensors be spectrally filtered. The different procedural sequences here arise from the measuring setups described in relation to the device according to the invention, wherein, for example, a polychromatic light-emitting light source is combined with color-selective filters, or a pulsed RGB light source is combined with a monochromatic receiver, which in varying time intervals correspondingly receives light with varying wavelengths.

Apart from the mentioned use of the optical measuring device for determining the type of surface to be processed, the optical measuring device can likewise be used to detect a stairway or the like. As the distance between the surface to be detected and the optical measuring device increases, the reflection point of the light emitted by the light source migrates out of the reception area of the light sensor. As a result, the evaluator and controller of the device can conclude that the device is located in front of a staircase going downstairs.

BRIEF DESCRIPTION OF THE DRAWINGS

The invention will be described in greater detail below based on an exemplary embodiment. Shown on:

FIG. 3: is a schematic side view of an optical measuring device (schematic sketch), FIG. 4: is a three-dimensional view of the optical measuring device.

DETAILED DESCRIPTION OF THE EMBODIMENTS

Figure 1:
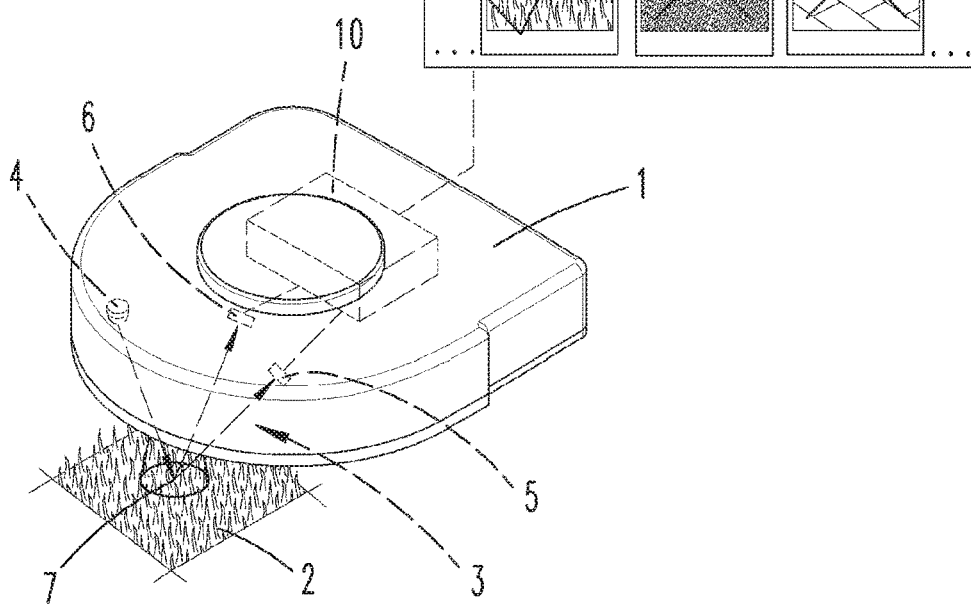
FIG. 1: is a vacuuming robot on a surface of a first kind.

FIG. 1 shows a device 1 according to the invention, which is here designed as a wiping robot. The device 1 is positioned on a schematically denoted surface 2, which is here a carpet. In order to detect the type of surface 2, the device 1 has an optical measuring device 3, which comprises a light source 4, a first light sensor 5 as well as a second light sensor 6. The aforementioned components of the optical measuring device 3 are arranged relative to each other in such a way that light emitted by the light source 4 is reflected on a reflection point 7 of the surface 2 and then hits the first light sensor 5. The second light sensor 6 is not arranged in the plane of incidence 8 spanned by the first light sensor 5, the light source 4 and the reflection point 7, but rather in a secondary plane 9 arranged perpendicular thereto and to the surface 2.

The device 1 also has an evaluator and controller 10, which controls the functions of the light source 4 and light sensors 5, 6 on the one hand, and accesses a memory having reference intensities for known surfaces on the other. As schematically depicted, the memory contains the reference intensities for carpets, wood floors, tiling and the like. Based on the light intensities measured with the light sensors 5, 6, the controller and evaluator 10 detects that the surface 2 is a carpet.

Figure 2:
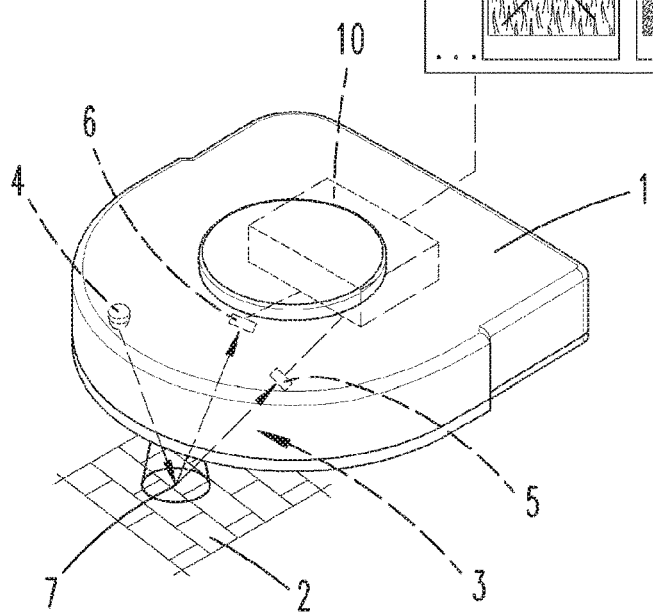
FIG. 2: is the vacuuming robot on a surface of a second kind.

FIG. 2 shows the device 1 on another surface 2, specifically a tile floor here. As explained above, the controller and evaluator 10 controls the optical measuring device 3 in such a way that the first light sensor 5 and the second light sensor 6 measure light intensities, which can then be compared with reference intensities. After the comparison, the controller and evaluator 10 here arrives at the conclusion that the surface 2 is a tile floor.

The schematic side view on FIG. 3 shows the optical measuring device 3, which has the first light sensor 5, the second light sensor 6 as well as the light source 4. The light source 4 along with the first light sensor 5 are arranged according to the principle "Angle of incidence α=Angle of reflection β"

in such a way that light emitted by the light source 4 is reflected on the reflection point 7 of the surface 2 and directly hits the first light sensor 5. Corresponding openings 11 for the light to pass through are formed in the housing of the device 1, the underside of which is shown here. Apart from the reflected light component, there further exists a diffusely scattered light component, the intensity of which depends on the composition of the surface 2. For example, if a rough, non-reflective surface 2 is involved, the scattered light component is higher than in the case of a smooth, reflective surface 2. The second light sensor 6 for measuring this scattered light component is not arranged in the plane of incidence 8, but rather in a secondary plane 9 that stands perpendicular to the plane of incidence 8 as well as perpendicular to the surface 2. If necessary, the second light sensor 6 also measures a component of an ambient light, for example which stems from ceiling lights in the room. As shown, the first light sensor 5 and the second light sensor 6 are advantageously arranged in a shared plane, which is aligned parallel to the surface 2.

FIG. 4 shows a three-dimensional view of the optical measuring device 3. Depicted is the plane of incidence 8 in which the light source 4, the reflection point 7 as well as the first light sensor 5 are arranged. Standing perpendicular thereto is the secondary plane 9, which intersects the second light sensor 6 along with the reflection point 7. In addition, the light source 4, the first light sensor 5 as well as the second light sensor 6 are arranged in a shared plane, which is aligned parallel to the surface 2. The angle of incidence α of the light emitted by the light source onto the surface 2, the angle of reflection β along with the angle γ between the surface 2 and a straight line running through the reflection point 7 and the second sensor 6 are even. As evident, the plane of incidence 8 and the secondary plane 9 are arranged at an angle δ of 90 degrees to each other.

In order to determine the type of surface 2, the optical measuring device 3 is operated in a measuring cycle that consists of three different measuring steps. In a first measuring step, the light source 4 is turned off, so that the first light sensor 5 and the second light sensor 6 exclusively detect any ambient light. In a second measuring step, the light source 4 is turned on, and the light intensity is exclusively measured with the first light sensor 5. In a third measuring step, the light source 4 is also turned on. However, the light intensity is now only measured with the second light sensor. Even though the measuring steps are here marked 1, 2 and 3, this does not connote a specific sequence.

Rather, it is irrelevant which of the three measuring steps is performed first, as long as the indicated conditions relating to the activity of the light source 4 or light sensors 5, 6 are satisfied.

In the first measuring step explained above, the first light sensor 5 and the second light sensor 6 are used to measure the light intensity of any ambient lighting:

$$I_{ambient}=I_1=I_2.$$

In the discussed second measuring step, the ambient light intensity along with the diffuse scatter and the radiation reflected by the reflection point 7 are measured:

$$I_3=I_{total}=I_{ambient}+I_{diffuse}+I_{reflected}.$$

Finally, in the third measuring step, the intensity of the ambient light as well as the intensity of the diffuse scatter are measured:

$$I_4=I_{ambient}+I_{diffuse}.$$

The light intensity of the diffuse scatter is derived as the solution to the equation system:

$$I_{diffuse}=I_4-I_1.$$

As well as the light intensity of the reflected radiation:

$$I_{reflected}=I_3-I_4.$$

These intensities can be compared with reference intensities for known surfaces 2.

For example, the reference intensities stored in a memory of the device 1 are light intensities that were measured during a corresponding measurement on carpet, parquet, laminate, tiles, etc. The evaluator and controller 10 of the device 1 compares these reference intensities with the intensities currently measured by the light sensors 5, 6, and given a correlation between the intensity values, can infer the type of surface 2 currently under the device 1. For example, the device 1 here arrives at the conclusion that the surface 2 to be determined is a tile floor.

In addition to the statements made above, let it be noted that the so-called reflection point 7 in practice does not involve a singular point, but rather a finitely expanded surface. This stems solely from the fact that the light emitted by the light source 4 is a light beam, which has a finite cross section and potentially even expands in the propagation direction. Beyond that, let it be mentioned that the Phong illumination model used for determining the type of surface 2 does not involve exact intensity calculations, but rather an empirically derived model that does not correctly reflect the physical circumstances inside of the optical measuring device 3. However, it has been demonstrated that determining the type of surface 2 according to this model leads to a reliable result.

REFERENCE LIST

1 Device
2 Surface
3 Measuring device
4 Light source
5 First light sensor
6 Second light sensor
7 Reflection point
8 Plane of incidence
9 Secondary plane
10 Controller and evaluator
11 Openings
α Angle of incidence
β Angle of reflection
γ Angle
δ Angle

The invention claimed is:

1. A method for cleaning a surface with a cleaning device, comprising:
  determining with an optical measuring device a type of the surface to be cleaned, and
  adjusting cleaning processes of the cleaning device based on the determined type of surface,
  wherein the step of determining comprises the following steps:
  radiating light inside of a plane of incidence at an angle of incidence (α) from a light source onto a reflection point of the surface,
  reflecting the light with a corresponding angle of reflection (β) to a first light sensor,
  arranging a second light sensor in a secondary plane that stands perpendicular to the surface, intersects the reflection point, and has an angle (δ) of between 80° and 100° to the plane of incidence in such a way that a straight line running through the reflection point and the second light sensor has an angle (γ) to the surface that is essentially as large as the angle of incidence (α) or the angle of reflection (β), and
  measuring with the first and second light sensors the light radiated by the light source,
  wherein the step of measuring comprises:
    measuring light intensity with the first light sensor and the second light sensor with the light source turned off,
    measuring the light intensity with the first light sensor with the light source turned on, and
    measuring the light intensity with the second light sensor with the light source turned on.

2. The method according to claim 1, further comprising the step of comparing the light intensities measured by the light sensors with corresponding reference intensities for known surfaces.

3. The method according to claim 1, wherein the light source emits polychromatic light.

4. The method according to claim 1, further comprising the step of spectrally filtering light traveling from the surface to the light sensors.

* * * * *